United States Patent
Chen et al.

(10) Patent No.: US 10,703,724 B2
(45) Date of Patent: Jul. 7, 2020

(54) CRYSTALLINE FORMS OF {[5-(3-CHLOROPHENYL)-3-HYDROXYPYRIDINE-2-CARBONYL] AMINO} ACETIC ACID AND PROCESSES FOR PREPARATION THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Po Zou, Suzhou (CN); Jinqiu Wang, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/468,848

(22) PCT Filed: Dec. 13, 2017

(86) PCT No.: PCT/CN2017/115909
§ 371 (c)(1),
(2) Date: Jun. 12, 2019

(87) PCT Pub. No.: WO2018/108101
PCT Pub. Date: Jun. 21, 2018

(65) Prior Publication Data
US 2020/0095203 A1    Mar. 26, 2020

(30) Foreign Application Priority Data
Dec. 13, 2016  (CN) .......................... 2016 1 1148362

(51) Int. Cl.
*C07D 213/81* (2006.01)
(52) U.S. Cl.
CPC ........ *C07D 213/81* (2013.01); *C07B 2200/13* (2013.01)
(58) Field of Classification Search
CPC .................................................. C07D 213/81
USPC ....................................................... 546/290
See application file for complete search history.

(56) References Cited

U.S. PATENT DOCUMENTS

| 7,811,595 B2* | 10/2010 | Kawamoto | C07D 405/10 424/401 |
| 2007/0299086 A1* | 12/2007 | Kawamoto | A61P 17/02 514/256 |
| 2012/0309977 A1* | 12/2012 | Lanthier | C07D 213/79 546/282.4 |

FOREIGN PATENT DOCUMENTS

| CN | 101506149 A | | 8/2009 | |
| CN | 105837502 | * | 8/2016 | .......... C07D 213/81 |
| CN | 105916502 A | | 8/2016 | |
| WO | 2012/170377 A1 | | 12/2012 | |
| WO | WO-2015073779 A1 | * | 5/2015 | .............. A61K 9/48 |
| WO | 2016/153996 A1 | | 9/2016 | |

OTHER PUBLICATIONS

European Search Opinion for Application No. EP 17881314.3, dated Dec. 4, 2019, 4 pages. (Year: 2019).*
Caira; "Crystalline Polymorphism of Organic Compounds", Top Curr Chem 1998, 198, 163-208. (Year: 1998).*
Pergola; Kidney International 2016, 90, 1115-1122. (Year: 2016).*
International Search Report for Application No. PCT/CN2017/115909, dated Mar. 19, 2018, 10 pages.

* cited by examiner

*Primary Examiner* — Daniel R Carcanague
(74) *Attorney, Agent, or Firm* — McCarter & English, LLP; Steven G. Davis; Wei Song

(57) ABSTRACT

The present disclosure relates to novel crystalline forms of {[5-(3-chlorophenyl)-3-hydroxypyridine-2-carbonyl] amino} acetic acid and processes for preparation and uses thereof. Crystalline form CS1, form CS2 and form CS8 of the present disclosure can be used for preparing drugs treating anemia, which providing new choices for preparing drugs of {[5-(3-chlorophenyl)-3-hydroxypyridine-2-carbonyl] amino} acetic acid, and having very important value for drug development.

20 Claims, 8 Drawing Sheets (I)

CRYSTALLINE FORMS OF {[5-(3-CHLOROPHENYL)-3-HYDROXYPYRIDINE-2-CARBONYL] AMINO} ACETIC ACID AND PROCESSES FOR PREPARATION THEREOF

CROSS-REFERENCE TO RELATED APPLICATIONS

This application is a U.S. national stage application of the PCT International Application No. PCT/CN2017/115909 filed on Dec. 13, 2017, which claims the benefit of foreign priority of Chinese patent application No. 201611148362.0 filed on Dec. 13, 2016. The entire contents of the aforementioned applications are incorporated herein by reference.

TECHNICAL FIELD

The present disclosure relates to technical field of pharmaceutical crystal, particularly relates to novel crystalline forms of {[5-(3-chlorophenyl)-3-hydroxypyridine-2-carbonyl] amino} acetic acid, processes for preparation and use thereof, belonging to the field of medicine.

BACKGROUND

Anemia may be chronic (e.g., anemia due to chronic kidney disease, anemia due to chronic heart failure, idiopathic anemia of aging, anemia of chronic disease, such as inflammatory bowel disease or rheumatoid arthritis, myelodysplastic syndrome, bone marrow fibrosis, and other aplastic or dysplastic anemias), subacute (e.g., chemotherapy induced anemia, such as chemotherapy for treating cancer, hepatitis C, or other chronic disease that reduces bone marrow production), acute (e.g., blood loss from injury or surgery), nutrition related (e.g., iron deficiency or vitamin B12 deficiency), or hemaglobinpathies (e.g., sickle cell disease, thalassemia, etc.). Hypoxia inducible factor (HIF) prolyl hydroxylase inhibitor is a novel drug for treating anemia. These drugs work by stabilizing HIF compounds and stimulating endogenous erythropoietin.

{[5-(3-chlorophenyl)-3-hydroxypyridine-2-carbonyl] amino} acetic acid, known as vadadustat, is developed by Akebia. vadadustat is an HIF prolyl hydroxylase inhibitor and has the function of treating or preventing anemia. The clinical trial of vadadustat for treatment of anemia due to chronic kidney disease is in Phase III. Its structure is shown in Formula (I).

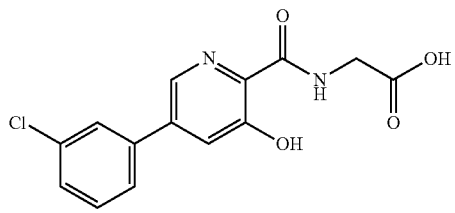

Formula (I)

Different crystalline forms of solid chemical drugs can lead to differences in their solubility, stability, flowability and compressibility, thereby affecting the safety and efficacy of pharmaceutical products containing the compounds (see K. Knapman, *Modern Drug Discovery*, 3, 53-54, 57, 2000.), which resulting in differences in clinical efficacy. The discovery of new crystalline forms (including anhydrates, hydrates, solvates, etc.) of the active pharmaceutical ingredients may provide drug substance with processing advantages and better physical and chemical properties such as better bioavailability, better storage stability, easiness to process, and easiness to purify. Some novel crystalline forms may serve as intermediate crystal forms to facilitate solid state transformation to desired forms. Novel polymorphs of raw materials can enhance the performance of the drug and provide more solid states in the formulation, such as improving dissolution and storage life, and making it easier to process.

Crystalline Form A, Form B and Form C of vadadustat were disclosed in WO2015073779. As disclosed in the specification, Form B is metastable and may convert to Form A in slurry at high temperature. It is found by the inventors of the present disclosure that the preparation repeatability of Form C is poor. WO2015073779 also disclosed that form A is suitable for the preparation of pharmaceutical formulations. However, other important properties such as stability and solubility in biological media were not mentioned. Therefore, it is still necessary to systematically develop different crystalline forms of vadadustat, to find novel crystalline forms more suitable for drug development, and to promote the preparation of better pharmaceutical formulations of the active pharmaceutical ingredients.

The present disclosure provides crystalline form CS1, form CS2 and Form CS8. Crystalline forms of the present disclosure can be easily made and have advantages in stability, hygroscopicity, solubility, mechanical stability, pressure stability, formulation stability and processing performance, which provides new and better choices for the preparation of pharmaceutical formulations containing vadadustat and is of great significance for drug development.

SUMMARY

The main objective of the present disclosure is to provide novel crystalline forms of vadadustat, processes for preparation and use thereof.

According to the objective of the present disclosure, crystalline form CS1 of vadadustat is provided (hereinafter referred to as Form CS1). Form CS1 is an anhydrate.

The X-ray powder diffraction pattern of Form CS1 shows characteristic peaks at 2theta values of 13.9°±0.2°, 15.3°±0.2°, 15.6°±0.2° and 26.8°±0.2° using CuKα radiation.

Further, the X-ray powder diffraction pattern of Form CS1 shows one or more characteristic peaks at 2theta values of 17.0°±0.2°, 19.1°±0.2°, 23.5°±0.2° and 25.6°±0.2°.

Furthermore, the X-ray powder diffraction pattern of Form CS1 shows characteristic peaks at 2theta values of 17.0°±0.2°, 19.1°±0.2°, 23.5°±0.2° and 25.6°±0.2°.

In a preferred embodiment, the X-ray powder diffraction pattern of Form CS1 shows characteristic peaks at 2theta values of 13.9°±0.2°, 15.3°±0.2°, 15.6°±0.2, 17.0°±0.2°, 19.1°±0.2°, 23.5°±0.2°, 25.6°±0.2° and 26.8°±0.2° using CuKα radiation.

Without any limitation being implied, in a specific embodiment, the X-ray powder diffraction pattern of Form CS1 is substantially as depicted in FIG. 1.

Without any limitation being implied, in a specific embodiment, the TGA curve of Form CS1 is substantially as depicted in FIG. 2, which shows about 1.3% weight loss when heated to 168° C.

Without any limitation being implied, in a specific embodiment, the ¹H NMR spectrum of Form CS1 is substantially as depicted in FIG. 3.

According to the objective of the present disclosure, the preparation method of Form CS1 of vadadustat is provided, and said method is 1) or 2):

1) Dissolving vadadustat into a single solvent of ethers and then evaporating at room temperature to obtain solids; or
2) Dissolving vadadustat into tetrahydrofuran, and then adding water into the solution or adding the solution into water slowly. Stirring at room temperature for a period of time. Filtering and drying to obtain solids.

Wherein, said ether is methyl tert-butyl ether; Said stirring time is 1-48 h, preferably 24 h.

Form CS1 of the present disclosure has the following advantages:

High solubility. Form CS1 was suspended in SGF (simulated gastric fluids) to obtain saturated solutions. After being equilibrated for 1 h, 4 h and 24 h, concentrations of the saturated solutions are all higher than those of Form A in WO2015073779. Drugs with low solubility often require high doses to reach therapeutic plasma concentration after oral administration. The increase in the solubility of the crystalline form CS1 can reduce the dose of the drug while ensuring the efficacy of the drug, thereby reducing the side effects of the drug and improving the safety of the drug. At the same time, the improvement of solubility of Form CS1 reduces the difficulty of formulation preparation, which is conducive to industrial production.

Good stability. Form CS1 is stable for at least 1 month when stored under the conditions of 25° C./60% RH and 40° C./75% RH. The better stability of Form CS1 can reduce the risk of drug dissolution rates and bioavailability change due to the change of crystalline forms, which is of great significance to ensure the efficacy and safety of drugs and prevent adverse drug reactions. Form CS1 with better stability is controllable during the crystallization process and not easy to produce mixed crystal. Meanwhile, during the formulation and storage processes, crystalline form with better stability is hard to convert into other crystal forms. As a result, consistent and controllable of product quality can be ensured, and the dissolution profile will not change with the storage time.

According to the objective of the present disclosure, crystalline form CS2 of vadadustat is provided (hereinafter referred to as Form CS2). Form CS2 is a hydrate.

The X-ray powder diffraction pattern of Form CS2 shows characteristic peaks at 2theta values of 14.1°±0.2°, 15.0°±0.2° and 18.3°±0.2° using CuKα radiation.

Further, the X-ray powder diffraction pattern of Form CS2 shows one or two or three characteristic peaks at 2theta values of 12.6°±0.2°, 13.4°±0.2° and 22.0°±0.2°.

Preferably, the X-ray powder diffraction pattern of Form CS2 shows characteristic peaks at 2theta values of 12.6°±0.2°, 13.4°±0.2° and 22.0°±0.2°.

Furthermore, the X-ray powder diffraction pattern of Form CS2 shows one or two or three characteristic peaks at 2theta values of 10.9°±0.2°, 16.1°±0.2° and 20.1°±0.2°.

Preferably, the X-ray powder diffraction pattern of Form CS2 shows characteristic peaks at 2theta values of 10.9°±0.2°, 16.1°±0.2° and 20.1°±0.2°.

In a preferred embodiment, the X-ray powder diffraction pattern of Form CS2 shows characteristic peaks at 2theta values of 10.9°±0.2°, 12.6°±0.2°, 13.4°±0.2°, 14.1°±0.2°, 15.0°±0.2°, 16.1°±0.2°, 18.3°±0.2°, 20.1°±0.2° and 22.0°±0.2° using CuKα radiation.

Without any limitation being implied, in a specific embodiment, the X-ray powder diffraction pattern of Form CS2 is substantially as depicted in FIG. 4.

Without any limitation being implied, in a specific embodiment, the DSC curve of Form CS2 is substantially as depicted in FIG. 5, which shows an endothermic peak when heated to about 85° C.

Without any limitation being implied, in a specific embodiment, the TGA curve of Form CS2 is substantially as depicted in FIG. 6, which shows about 5.5% weight loss when heated to 111° C.

Without any limitation being implied, in a specific embodiment, the ¹H NMR spectrum of Form CS2 is substantially as depicted in FIG. 7.

According to the objective of the present disclosure, the preparation method of Form CS2 of vadadustat is provided, and said method is:

Dissolving vadadustat into a solvent selected from the group consisting of ketones, 1,4-dioxane and dimethyl sulfoxide (DMSO), and then adding water into the solution slowly or adding the solution into water. Stirring at room temperature for a period of time. Filtering and drying to obtain solids.

Preferably, said ketone is acetone;

Preferably, said stirring time is 1-48 h, more preferably 24 h.

Form CS2 of the present disclosure has the following advantages:

Good stability. Form CS2 has better stability than Form A of WO2015073779 in water. Form CS2 is stable for at least 1 month when stored under the conditions of 25° C./60% RH, 40° C./75% and 60° C./75% RH. The crystal structure of Form CS2 doesn't change after manual grinding. The better stability of Form CS2 can reduce the risk of drug dissolution rates and bioavailability change due to the change of crystalline forms. It is of great significance to ensure the efficacy and safety of drugs and to prevent the occurrence of adverse drug reactions. Form CS2 with better stability is controllable during the crystallization process and not easy to produce mixed crystal. Meanwhile, during the formulation and storage processes, crystalline form with better stability is hard to convert into other crystal forms. As a result, consistent and controllable of product quality can be ensured, and the dissolution profile will not change with the storage time. Meanwhile, Form CS2 has better mechanical stability. The crystalline drug with better mechanical stability has low requirements on the crystallization equipment, and no special post-treatment condition is required. It is more stable in the formulation process, can significantly reduce the development cost of the drug products, enhances the quality of the drug, and has strong economic value.

Low hygroscopicity. Form CS2 has low hygroscopicity. The weight gain of Form CS2 from 40% RH to 80% RH is 0.11%. The drug products of Form CS2 with low hygroscopicity do not require special packaging and storage conditions, which is conducive to the long-term storage of drugs and will greatly reduce the cost of packaging, storage and quality control. The crystalline form with low hygroscopicity doesn't require special drying conditions during the preparation process, which simplifies the preparation and post-treatment process of the drug, is easy for industrial production, and reduces the cost of drug research and development.

Good pressure stability. Form CS2 is stable after tableting under 3 KN, 7 KN, 14 KN. From the perspective of product quality, failure in hardness/friability test and tablet crack issue can be avoided in the tableting process due to better pressure stability of Form CS2, and reduce the requirements for the pretreatment process (such as particle size control in raw material milling, water content control during drying process, particle size and particle size distribution control). Good pressure stability makes the preparation process simpler, and improves product appearance and product quality. From the perspective of production efficiency and cost, good pressure stability of Form CS2 can improve the speed of tableting and production efficiency. There is no need to use some expensive special excipients in the process to improve pressure stability, which reduces the cost of excipients. In addition, the feasibility of direct tableting of Form CS2 is increased which greatly simplifies the process of preparation and reduces the cost of development and production. From the perspective of patient compliance, Form CS2 has good pressure stability, and can be further made into tablets. Compared with other dosage forms, tablets are smaller in volume and are more convenient to carry and take, which can improve patient compliance.

Good stability of drug product. Form CS2 in tablets is table for at least 3 months under 30° C./60% RH. Drug product of Form CS2 has good stability, so no strict requirement is needed for packaging and storage, which is beneficial to long-term storage. The cost of storage and quality control will be greatly reduced. Form CS2 drug product can keep physically and chemically stable during process of preparation of formulation, which is beneficial to production, packaging, storage and transportation of drugs, and can also ensure the quality of the product, and is convenient to industrial production.

According to the objective of the present disclosure, crystalline form CS8 of vadadustat is provided (hereinafter referred to as Form CS8). Form CS8 is an anhydrate.

The X-ray powder diffraction pattern of Form CS8 shows characteristic peaks at 2theta values of 21.2°±0.2°, 22.6°±0.2° and 26.8°±0.2° using CuKα radiation.

Furthermore, the X-ray powder diffraction pattern of Form CS8 shows one or more characteristic peaks at 2theta values of 13.5°±0.2°, 13.9°±0.2°, 15.8°±0.2°, 21.9°±0.2° and 28.7°±0.2°.

Preferably, the X-ray powder diffraction pattern of Form CS8 shows characteristic peaks at 2theta values of 13.5°±0.2°, 13.9°±0.2°, 15.8°±0.2°, 21.9°±0.2° and 28.7°±0.2°.

In a preferred embodiment, the X-ray powder diffraction pattern of Form CS8 shows characteristic peaks at 2theta values of 13.5°±0.2°, 13.9°±0.2°, 15.8°±0.2°, 21.2°±0.2°, 21.9°±0.2°, 22.6°±0.2°, 26.8°±0.2° and 28.7°±0.2° using CuKα radiation.

Without any limitation being implied, in a specific embodiment, the X-ray powder diffraction pattern of Form CS8 is substantially as depicted in FIG. 8.

Without any limitation being implied, in a specific embodiment, the DSC curve of Form CS8 is substantially as depicted in FIG. 9.

According to the objective of the present disclosure, the preparation method of Form CS8 of vadadustat is provided, and said method is:

Dissolving vadadustat into a mixture of water and ketones at a temperature 40-56° C. Placing the clear solution at 5° C. and stirring for a period of time. Filtering and drying to obtain solids.

Furthermore, said dissolving temperature is 50° C.;
Furthermore, said ketone is acetone;
Furthermore, said volume ratio of acetone and water is 1:3-2:1, preferably 6:7;
Furthermore, said stirring time is 8-48 h, preferably 16 h.

Form CS8 of the present disclosure has the following advantages:

High solubility. Form CS8 was suspended in SGF (simulated gastric fluids) and water to obtain saturated solutions. Concentrations of the saturated solutions are all higher than that of Form A in WO2015073779. Drugs with low solubility often require high doses to reach therapeutic plasma concentration after oral administration. Increased solubility of Form CS8 enables us to reduce the dosage of the drug while ensuring the efficacy of the drug, thereby reducing the side effects of the drug and improving the safety of the drug. At the same time, the improvement of solubility of Form CS8 reduces the difficulty of formulation preparation, which is conducive to industrial production.

Good stability. Form CS8 is stable for at least 20 days when stored under the conditions of 25° C./60% RH, 40° C./75% RH and 60° C./75% RH. Better stability of Form CS8 can reduce the risk of drug dissolution rates and bioavailability change due to the changes of crystalline forms. It is of great significance to ensure the efficacy and safety of drugs and prevent adverse drug reactions. Form CS8 with better stability is controllable during the crystallization process and not easy to produce mixed crystal. Meanwhile, during the formulation and storage processes, crystalline form with better stability is hard to convert into other crystal forms. As a result, consistent and controllable of product quality can be ensured Low hygroscopicity. The weight gain of Form CS8 at 80% RH is 0.06% and at 90% RH is 0.08%. Form CS8 is non hygroscopic or almost non hygroscopic. Form CS8 has low hygroscopicity, and its drug products do not require strict packaging and storage conditions, which is conducive to the long-term storage of drugs and will greatly reduce the cost of material packaging, storage and quality control. The low hygroscopicity of Form CS8 requires no special drying conditions in the preparation of drug products, simplifies the preparation and post-treatment process of drugs, and facilitates industrial production, and reduces the cost of drug research and development.

In the preparation method of Form CS1, Form CS2 and Form CS8 of the present disclosure:

Said "room temperature" refers to 10-30° C.

Said "evaporating" is accomplished by using a conventional method in the field such as slow evaporation or rapid evaporation. Rapid evaporation comprises dissolving compound in specific system, filtering, and evaporating rapidly in an open container. Slow evaporation comprises dissolving the compound in a specific system, filtering, covering the opening of the container with a sealing film, and making several pinholes on the film with a needle and evaporating slowly.

Said "stirring" is accomplished by using a conventional method in the field such as magnetic stirring or mechanical stirring and the stirring speed is 50 to 1800 r/min, preferably stirring speed is 300 to 900 r/min.

Unless otherwise specified, said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, forced air convection oven or vacuum oven.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS1, Form CS2 and Form CS8, of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

In addition, the present disclosure provides a pharmaceutical composition, said pharmaceutical composition comprises a therapeutically and/or prophylactically effective amount of one or more forms selected from Form CS1, Form CS2 and Form CS8, and at least one pharmaceutically acceptable excipients.

Further, Form CS1, Form CS2 and Form CS8 of the present disclosure can be used for preparing drugs treating anemia.

Furthermore, Form CS1, Form CS2 and Form CS8 of the present disclosure can be used for preparing drugs treating anemia caused by chronic kidney disease.

DETAILED DESCRIPTION

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

Instruments and Methods for Data Acquisition:

X-ray powder diffraction patterns in the present disclosure were acquired by a Bruker D2 PHASER X-ray powder diffractometer. The parameters of the X-ray powder diffraction method of the present disclosure were as follows:

X-ray Reflection: Cu, Kα
Kα1 (Å): 1.54060; Kα2 (Å): 1.54439
Kα2/Kα1 intensity ratio: 0.50
Voltage: 30 (kV)
Current: 10 (mA)
Scan range: from 3.0 degree to 40.0 degree Differential scanning calorimetry (DSC) data in the present disclosure were acquired by a TA Q2000. The parameters of the DSC method of the present disclosure were as follows:

Heating rate: 10° C./min
Purge gas: nitrogen

Thermal gravimetric analysis (TGA) data in the present disclosure were acquired by a TA Q5000. The parameters of the TGA method of the present disclosure were as follows:

Heating rate: 10° C./min
Purge gas: nitrogen

Dynamic Vapor Sorption (DVS) was measured via an SMS (Surface Measurement Systems Ltd.) intrinsic DVS instrument. Its control software is DVS-Intrinsic control software, and its analysis software is DVS-Intrinsic Analysis software. Typical Parameters for DVS test are as follows:

Temperature: 25° C.
Gas and flow rate: N2, 200 mL/min
dm/dt: 0.002%/min
RH range: 0% RH to 95% RH Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL. Unless otherwise specified, the following examples were conducted at room temperature.

EXAMPLE 1

Preparation of Form CS1

11.3 mg of vadadustat was weighted into a 1.5 mL glass vial and 0.5 mL of methyl tert-butyl ether (MTBE) was added into the vial to form a clear solution. Solid was obtained after evaporation at room temperature for two days.

Figure 1:
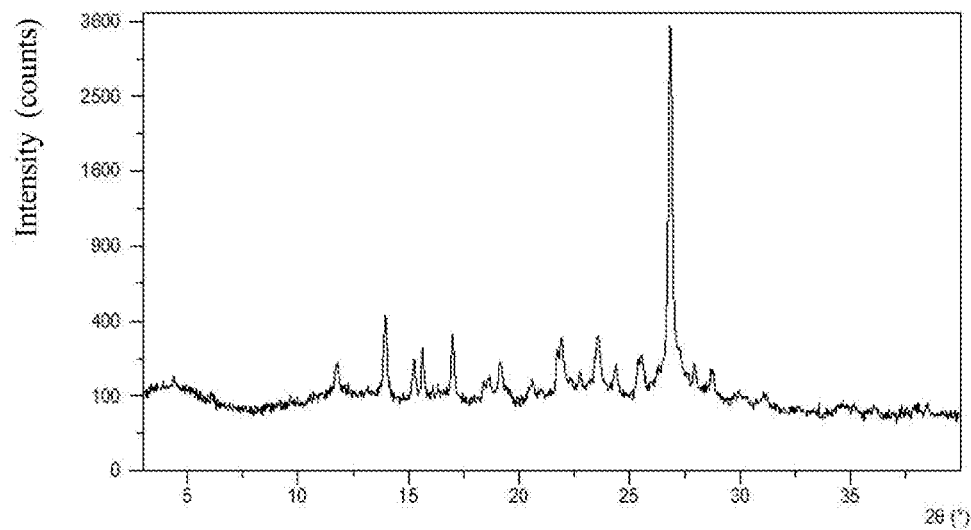
FIG. 1 shows an XRPD pattern of Form CS1 according to example 1 of the present disclosure.

According to the test results, the solid obtained in Example 1 was confirmed to be Form CS1. The XRPD data are listed in Table 1, and the XRPD pattern is depicted in FIG. 1.

Figure 2:
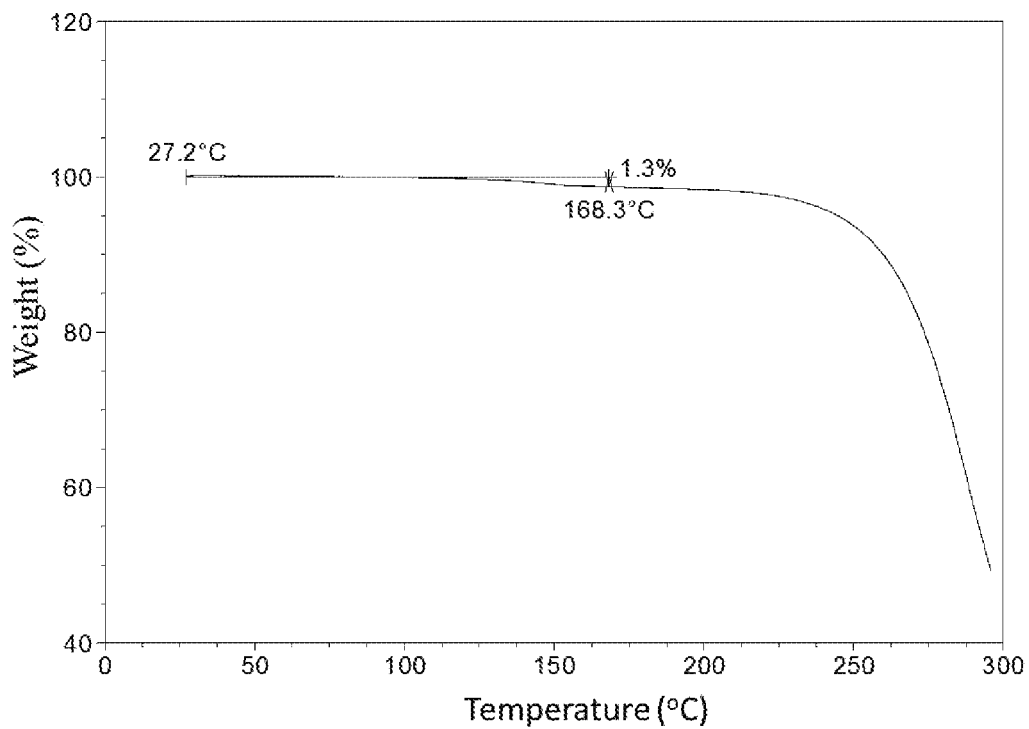
FIG. 2 shows a TGA curve of Form CS1 according to example 1 of the present disclosure.

The TGA curve of Form CS1 shows about 1.3% weight loss when heated to 168° C., which is depicted in FIG. 2.

Figure 3:
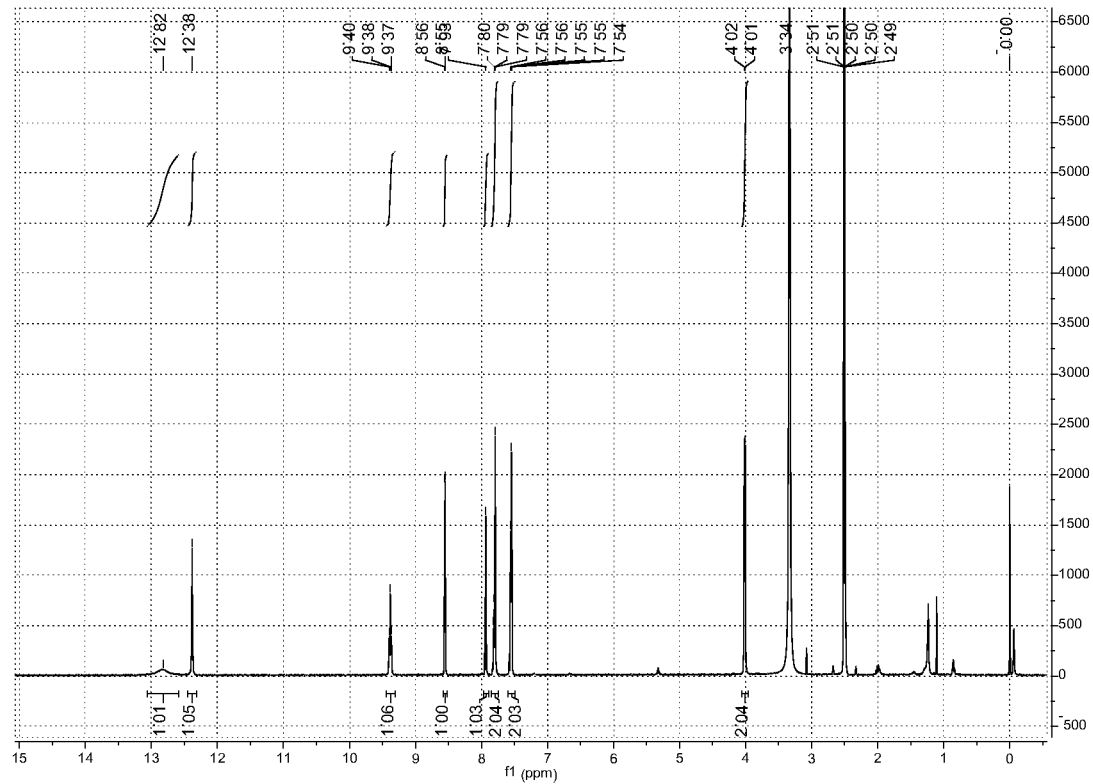
FIG. 3 shows a $^1$H NMR spectrum of Form CS1 according to example 1 of the present disclosure.

The $^1$H NMR spectrum of Form CS1 is depicted in FIG. 3, and the corresponding data are: $^1$H NMR (400 MHz, DMSO) δ 12.82 (s, 1H), 12.38 (s, 1H), 9.38 (t, J=6.1 Hz, 1H), 8.55 (d, J=1.9 Hz, 1H), 7.93 (s, 1H), 7.85-7.74 (m, 2H), 7.60-7.49 (m, 2H), 4.01 (d, J=6.2 Hz, 2H).

TABLE 1

| 2θ | d spacing | Intensity % |
|---|---|---|
| 11.79 | 7.51 | 3.37 |
| 13.95 | 6.35 | 10.11 |
| 15.26 | 5.81 | 4.02 |
| 15.62 | 5.67 | 5.28 |
| 17.00 | 5.22 | 6.99 |
| 19.10 | 4.65 | 3.51 |
| 21.72 | 4.09 | 5.21 |
| 21.95 | 4.05 | 7.03 |
| 23.55 | 3.78 | 7.32 |
| 24.37 | 3.65 | 3.87 |
| 25.56 | 3.49 | 4.43 |
| 26.82 | 3.32 | 100.00 |
| 27.91 | 3.20 | 3.99 |
| 28.78 | 3.10 | 3.29 |

EXAMPLE 2

Preparation of Form CS1

8.7 mg of vadadustat was weighted into a 1.5 mL glass vial and 0.1 mL of tetrahydrofuran (THF) was added into the vial to form a clear solution. The clear solution was slowly added into 1.5 mL of water under magnetic stirring, and then the system was stirred for 24 h at room temperature. Solid was obtained after filtration and drying.

According to the test results, the solid obtained in Example 2 was confirmed to be Form CS1. The XRPD data are listed in Table 2.

TABLE 2

| 2θ | d spacing | Intensity % |
|---|---|---|
| 11.83 | 7.48 | 4.31 |
| 13.94 | 6.35 | 5.12 |
| 15.27 | 5.80 | 2.57 |
| 15.66 | 5.66 | 2.94 |
| 17.07 | 5.20 | 3.35 |
| 18.64 | 4.76 | 2.37 |
| 19.13 | 4.64 | 2.98 |
| 21.78 | 4.08 | 5.85 |
| 23.57 | 3.77 | 7.28 |
| 25.54 | 3.49 | 3.45 |
| 26.83 | 3.32 | 100.00 |
| 28.77 | 3.10 | 2.29 |
| 35.15 | 2.55 | 0.72 |

EXAMPLE 3

Solubility of Form CS1

Certain amount of Form CS1 in the present disclosure and Form A in WO2015073779 were weighted into vials and suspended in SGF (Simulated Gastric Fluids). The systems were rotated on the rotator at a rate of 25 r/min. After equilibrated for 1 h, 4 h and 24 h, the suspension was separated through 0.45 μm PTFE centrifugal filter and the filtrate was collected. The concentration of the filtrates was measured by HPLC. The results are listed in Table 3.

TABLE 3

| | Solubility Solubility in SGF (mg/mL) | |
|---|---|---|
| Time | Form CS1 | Form A in WO2015073779 |
| 1 h | 0.023 | 0.0085 |
| 4 h | 0.026 | 0.0086 |
| 24 h | 0.019 | 0.0038 |

The results show that the solubility of Form CS1 in SGF at 1 h, 4 h and 24 h is higher than that of Form A in WO2015073779.

EXAMPLE 4

Stability of Form CS1

Form CS1 in the present disclosure was stored under 25° C./60% RH and 40° C./75% RH for 1 month. The XRPD pattern was collected before and after storage, and the XRPD pattern overlay is depicted in FIG. 10. The results are shown in Table 4.

TABLE 4

Figure 10A:
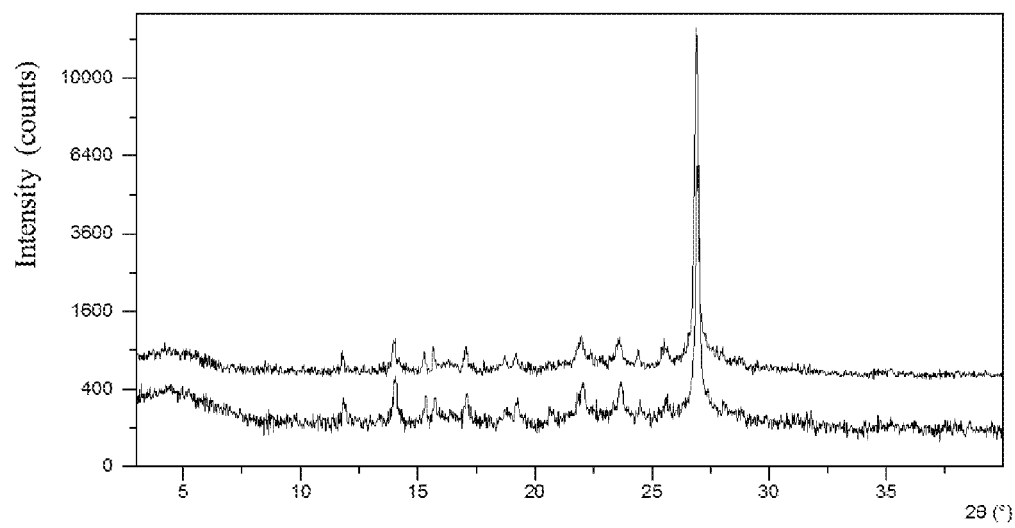
FIG. 10A shows an XRPD pattern overlay of Form CS1 of the present disclosure before and after being stored under 25° C./60% RH for one month (top: XRPD pattern before storage, bottom: XRPD pattern after storage).
Figure 10B:
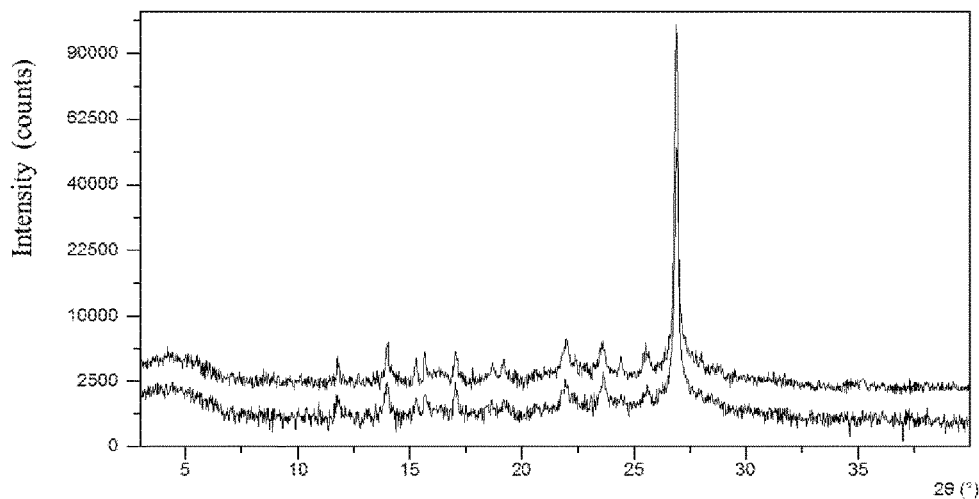
FIG. 10B shows an XRPD pattern overlay of Form CS1 of the present disclosure before and after being stored under 40° C./75% RH for one month (top: XRPD pattern before storage, bottom: XRPD pattern after storage).

| Initial Form | Condition | Time | Solid Form |
|---|---|---|---|
| Form CS1 | 25° C./60% RH | 1 month | Form CS1, no form change (as shown in FIG. 10A) |
| | 40° C./75% RH | 1 month | Form CS1, no form change (as shown in FIG. 10B) |

The results show that Form CS1 keeps stable for at least 1 month under 25° C./60% RH and 40° C./75% RH conditions. It can be seen that Form CS1 in the present disclosure has good stability.

EXAMPLE 5

Preparation of Form CS2

118.5 mg of vadadustat was weighted into a 3 mL glass vial and 1 mL of acetone was added into the vial to form a clear solution. The clear solution was slowly added into 15 mL of water under magnetic stirring, and then the solution was stirred for 24 h at room temperature. Solid was obtained after filtration and drying.

Figure 4:
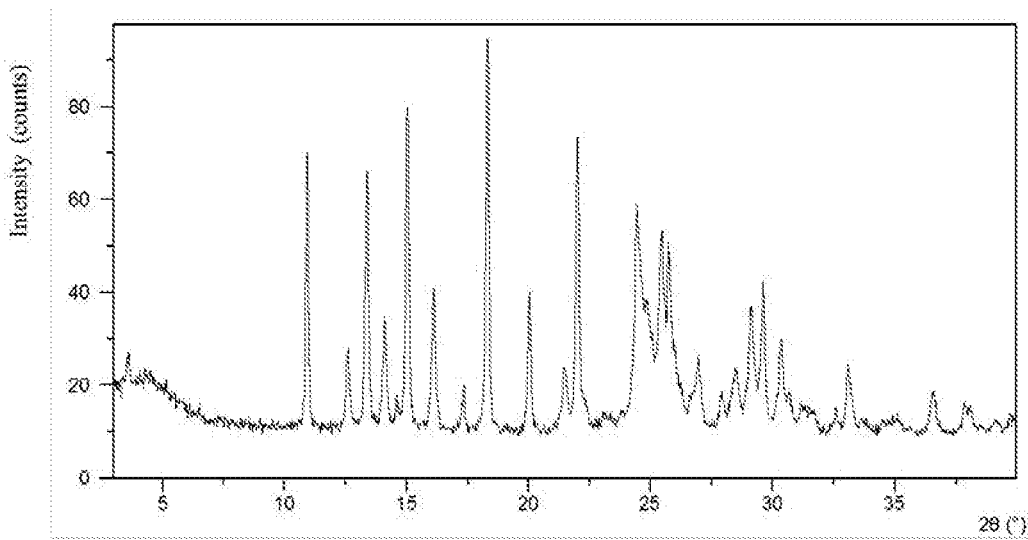
FIG. 4 shows an XRPD pattern of Form CS2 according to example 4 of the present disclosure.

According to the test results, the solid obtained in Example 5 was confirmed to be Form CS2. The XRPD data are listed in Table 5, and the XRPD pattern is depicted in FIG. 4.

Figure 5:
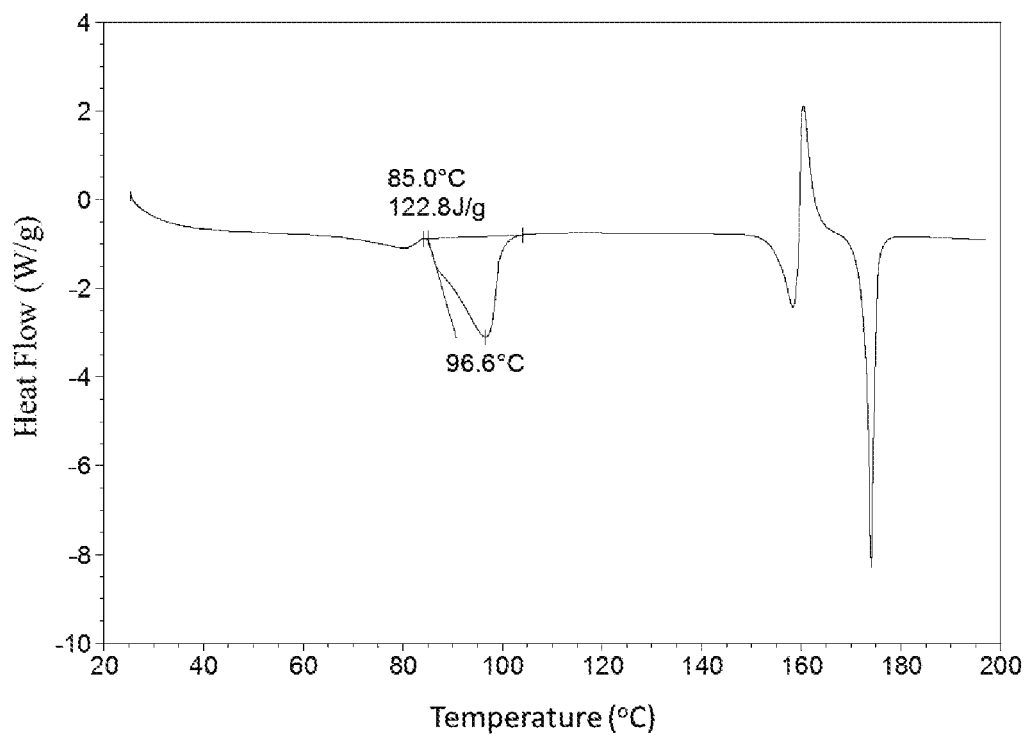
FIG. 5 shows a DSC curve of Form CS2 according to example 4 of the present disclosure.

The DSC curve of Form CS2 is depicted in FIG. 5. The endothermic peak at around 85° C. corresponds to the loss of water. Form CS2 is a hydrate.

Figure 6:
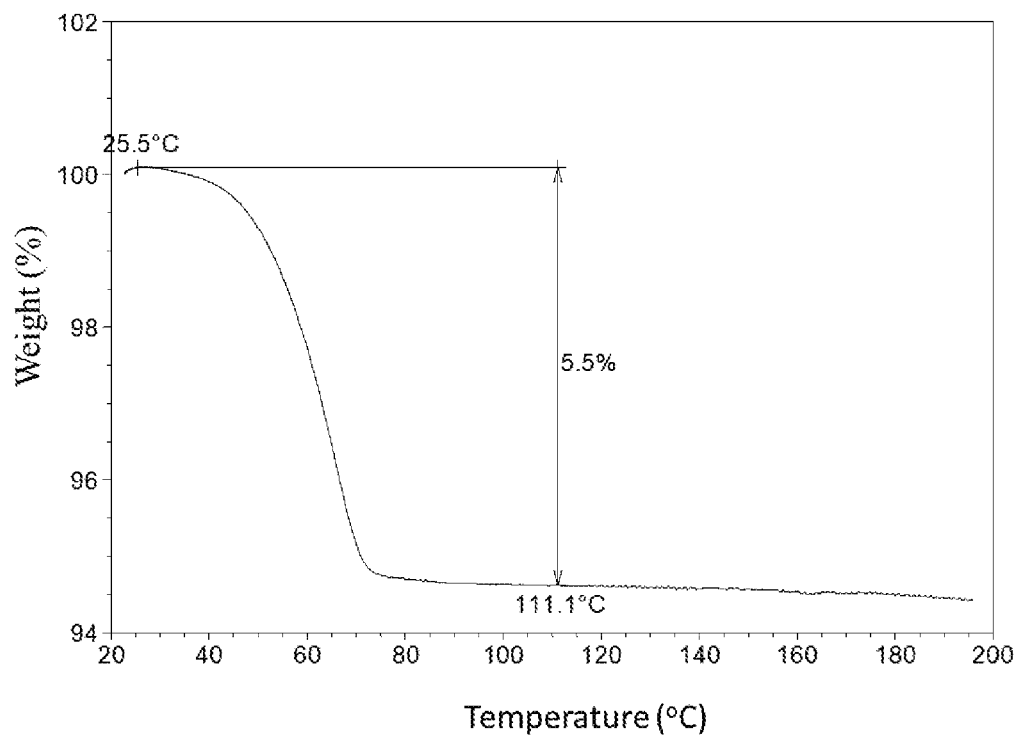
FIG. 6 shows a TGA curve of Form CS2 according to example 4 of the present disclosure.

The TGA curve of Form CS2 shows about 5.5% weight loss when heated to 111° C., which is depicted in FIG. 6. According to TGA result, one mole of Form CS2 contains about one mole of water.

Figure 7:
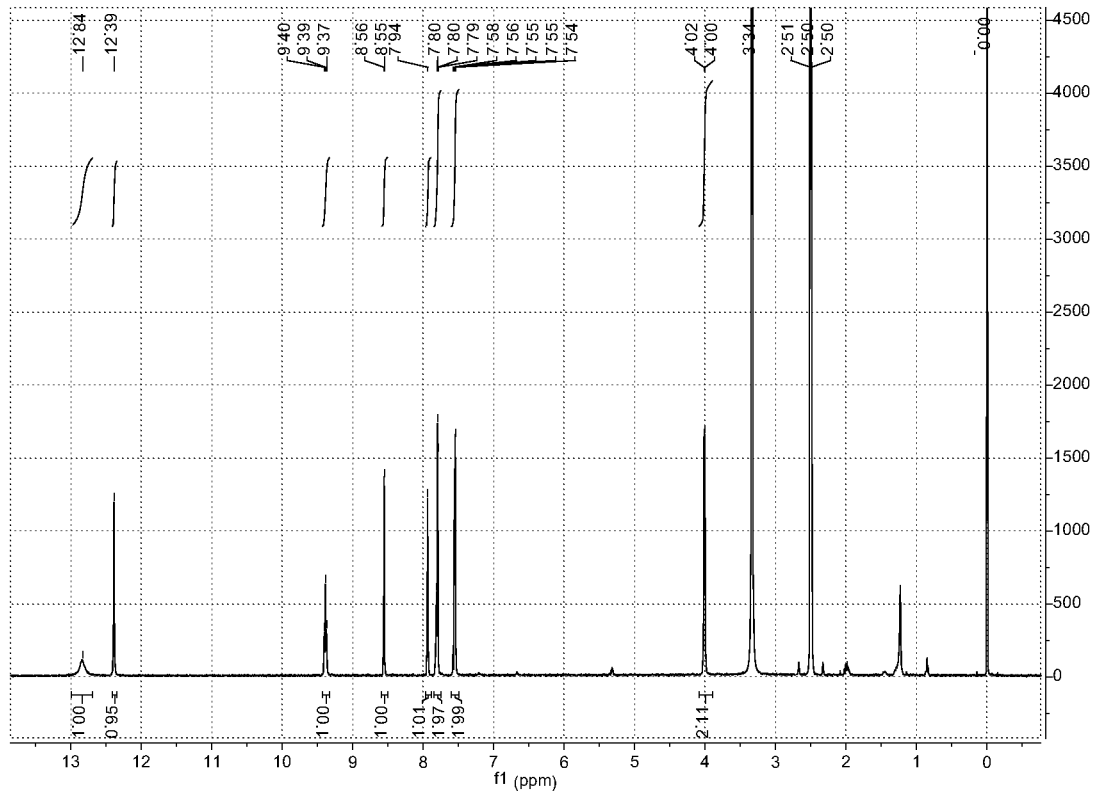
FIG. 7 shows a $^1$H NMR spectrum of Form CS2 according to example 4 of the present disclosure.

The $^1$H NMR spectrum of Form CS2 is depicted in FIG. 7, and the corresponding data are: $^1$H NMR (400 MHz, DMSO) δ 12.84 (s, 1H), 12.39 (s, 1H), 9.39 (t, J=6.1 Hz, 1H), 8.56 (d, J=1.9 Hz, 1H), 7.94 (s, 1H), 7.85-7.75 (m, 2H), 7.60-7.49 (m, 2H), 4.01 (d, J=6.2 Hz, 2H).

TABLE 5

| 2θ | d spacing | Intensity % |
|---|---|---|
| 3.63 | 24.32 | 8.43 |
| 10.95 | 8.08 | 66.50 |
| 12.60 | 7.03 | 19.75 |
| 13.38 | 6.62 | 67.46 |
| 14.10 | 6.28 | 28.25 |
| 14.59 | 6.07 | 7.96 |
| 15.04 | 5.89 | 82.04 |
| 16.10 | 5.50 | 36.21 |
| 17.34 | 5.11 | 10.89 |
| 18.31 | 4.84 | 100.00 |
| 20.05 | 4.43 | 35.62 |
| 21.45 | 4.14 | 15.25 |
| 21.99 | 4.04 | 71.74 |
| 24.44 | 3.64 | 56.69 |
| 25.43 | 3.50 | 49.03 |
| 25.77 | 3.46 | 45.28 |
| 26.97 | 3.31 | 18.18 |
| 27.92 | 3.20 | 8.99 |
| 28.48 | 3.13 | 16.19 |
| 29.13 | 3.07 | 31.71 |
| 29.61 | 3.02 | 38.37 |
| 30.36 | 2.94 | 22.90 |
| 31.47 | 2.84 | 5.28 |
| 32.58 | 2.75 | 4.08 |
| 33.08 | 2.71 | 16.59 |
| 34.96 | 2.57 | 3.05 |
| 36.61 | 2.45 | 10.14 |
| 37.96 | 2.37 | 5.46 |
| 39.15 | 2.30 | 2.87 |

EXAMPLE 6

Preparation of Form CS2

8.5 mg of vadadustat was weighted into a 1.5 mL glass vial and 0.075 mL of acetone was added into the vial to form a clear solution. The clear solution was slowly added into 1.5 mL of water under magnetic stirring, and then the system was stirred for 24 h at room temperature. Solid was obtained after filtration and drying.

According to the test results, the solid obtained in Example 6 was confirmed to be Form CS2. The XRPD data are listed in Table 6.

TABLE 6

| 2θ | d spacing | Intensity % |
|---|---|---|
| 3.62 | 24.41 | 10.56 |
| 10.94 | 8.09 | 61.20 |
| 12.60 | 7.02 | 5.16 |
| 13.40 | 6.61 | 17.01 |
| 14.09 | 6.28 | 7.31 |
| 14.62 | 6.06 | 8.05 |
| 15.06 | 5.88 | 18.83 |
| 16.11 | 5.50 | 12.39 |
| 18.32 | 4.84 | 100.00 |
| 20.08 | 4.42 | 11.34 |
| 21.52 | 4.13 | 9.31 |
| 22.02 | 4.04 | 77.03 |
| 24.63 | 3.61 | 11.58 |
| 25.48 | 3.50 | 8.60 |
| 25.80 | 3.45 | 18.90 |
| 27.01 | 3.30 | 3.42 |
| 27.90 | 3.20 | 3.13 |
| 28.47 | 3.13 | 3.45 |
| 29.14 | 3.06 | 6.91 |
| 29.63 | 3.02 | 20.38 |
| 30.37 | 2.94 | 6.25 |
| 31.50 | 2.84 | 1.81 |
| 33.08 | 2.71 | 9.66 |
| 35.01 | 2.56 | 1.43 |
| 36.63 | 2.45 | 3.74 |
| 38.03 | 2.37 | 2.39 |

EXAMPLE 7

Preparation of Form CS2

9.2 mg of vadadustat was weighted into a 1.5 mL glass vial and 0.1 mL of 1,4-dioxane was added into the vial to form a clear solution. 1.5 mL of water was slowly added into the clear solution under magnetic stirring, and then the system was stirred for 24 h at room temperature. Solid was obtained after filtration and drying.

According to the test results, the solid obtained in Example 7 was confirmed to be Form CS2. The XRPD data are listed in Table 7.

TABLE 7

| 2θ | d spacing | Intensity % |
|---|---|---|
| 3.65 | 24.22 | 13.30 |
| 10.94 | 8.09 | 58.16 |
| 12.61 | 7.02 | 3.77 |
| 13.38 | 6.62 | 16.57 |
| 14.11 | 6.28 | 6.10 |
| 14.66 | 6.04 | 5.85 |
| 15.05 | 5.89 | 26.10 |
| 16.12 | 5.50 | 11.93 |
| 17.33 | 5.12 | 4.33 |
| 18.32 | 4.84 | 100.00 |
| 20.07 | 4.43 | 16.14 |
| 21.54 | 4.13 | 9.59 |
| 22.04 | 4.03 | 71.63 |
| 24.53 | 3.63 | 16.59 |
| 25.44 | 3.50 | 11.92 |
| 25.76 | 3.46 | 23.96 |
| 27.88 | 3.20 | 4.79 |
| 28.48 | 3.13 | 4.57 |
| 29.10 | 3.07 | 9.35 |
| 29.63 | 3.01 | 22.22 |
| 30.35 | 2.95 | 9.30 |
| 31.32 | 2.86 | 4.35 |
| 33.10 | 2.71 | 11.03 |
| 34.91 | 2.57 | 1.94 |
| 36.63 | 2.45 | 5.98 |
| 37.98 | 2.37 | 3.20 |

EXAMPLE 8

Preparation of Form CS2

8.2 mg of vadadustat was weighted into a 1.5 mL glass vial and 0.05 mL of dimethyl sulfoxide (DMSO) was added into the vial to form a clear solution. 1.5 mL of water was slowly added into the clear solution under magnetic stirring, and then the system was stirred for 24 h at room temperature. Solid was obtained after filtration and drying.

According to the test results, the solid obtained in Example 8 was confirmed to be Form CS2. The XRPD data are listed in Table 8.

TABLE 8

| 2θ | d spacing | Intensity % |
|---|---|---|
| 3.56 | 24.78 | 14.42 |
| 10.93 | 8.09 | 75.55 |
| 12.64 | 7.00 | 7.88 |
| 13.41 | 6.60 | 25.33 |
| 14.12 | 6.27 | 13.27 |
| 14.68 | 6.04 | 8.56 |
| 15.13 | 5.86 | 25.16 |
| 16.15 | 5.49 | 16.80 |
| 17.36 | 5.11 | 5.49 |
| 18.32 | 4.84 | 100.00 |
| 20.05 | 4.43 | 22.61 |
| 22.02 | 4.04 | 73.20 |
| 24.49 | 3.63 | 34.96 |
| 25.80 | 3.45 | 35.47 |
| 26.98 | 3.30 | 6.55 |
| 28.50 | 3.13 | 9.04 |
| 29.14 | 3.06 | 17.18 |
| 29.65 | 3.01 | 30.41 |
| 30.36 | 2.94 | 12.75 |
| 33.09 | 2.71 | 12.79 |
| 34.83 | 2.58 | 2.66 |
| 36.61 | 2.45 | 10.66 |
| 37.95 | 2.37 | 4.69 |

EXAMPLE 9

Stability of Form CS2

Figure 13:
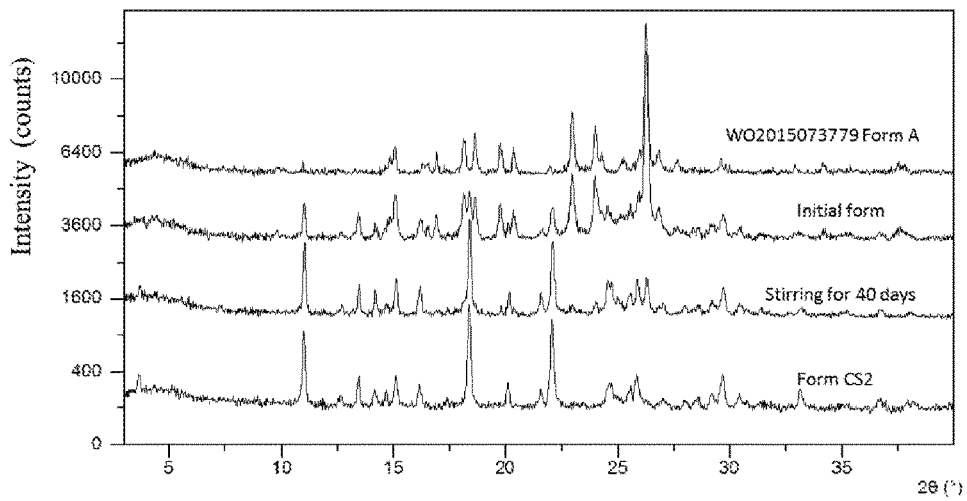
FIG. 13 shows an XRPD pattern overlay of Form CS2 and Form A of WO2015073779 in slurry.

Stability comparison experiment: about 4 mg of Form CS2 and Form A in WO2015073779 was weighted into a 1.5 mL glass vial and 1.0 mL of water was added into the vial. The solid form of the initial sample was tested. After stirring at a rate of 500 r/min at room temperature for about 40 days, the solid form of the sample was tested again. The XRPD pattern overlay is depicted in FIG. 13. The result shows that Form A in WO2015073779 almost completely converted to Form CS2 after 40 days of slurry, which means Form CS2 is more stable than Form A in WO2015073779 in water.

Accelerated experiment: Form CS2 was stored under 25° C./60% RH, 40° C./75% RH and 60° C./75% RH for 1 month. The XRPD pattern was collected before and after storage, and the overlay is depicted in FIG. 11. The results are shown in Table 9. The results show that Form CS2 keeps stable for at least 1 month under 25° C./60% RH, 40° C./75% RH and 60° C./75% RH conditions.

TABLE 9

Figure 11A:
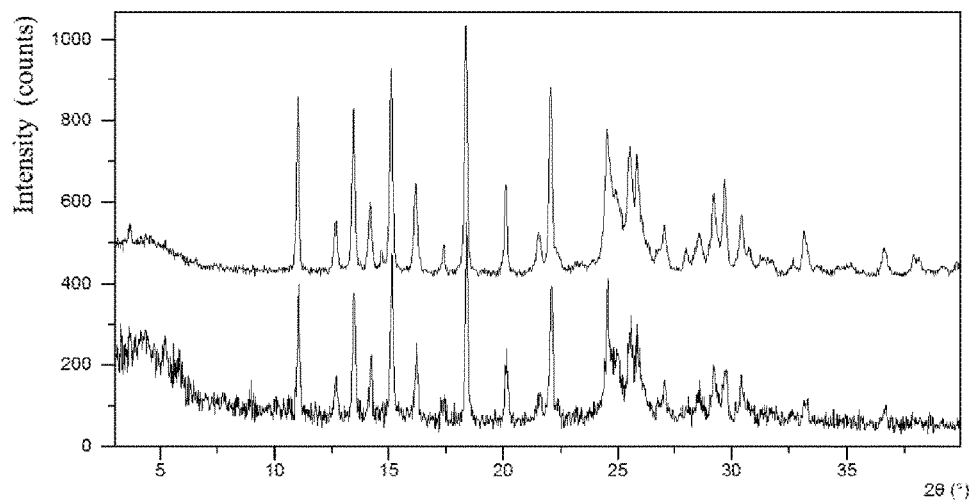
FIG. 11A shows an XRPD pattern overlay of Form CS2 of the present disclosure before and after being stored under 25° C./60% RH for one month (top: XRPD pattern before storage, bottom: XRPD pattern after storage).
Figure 11B:
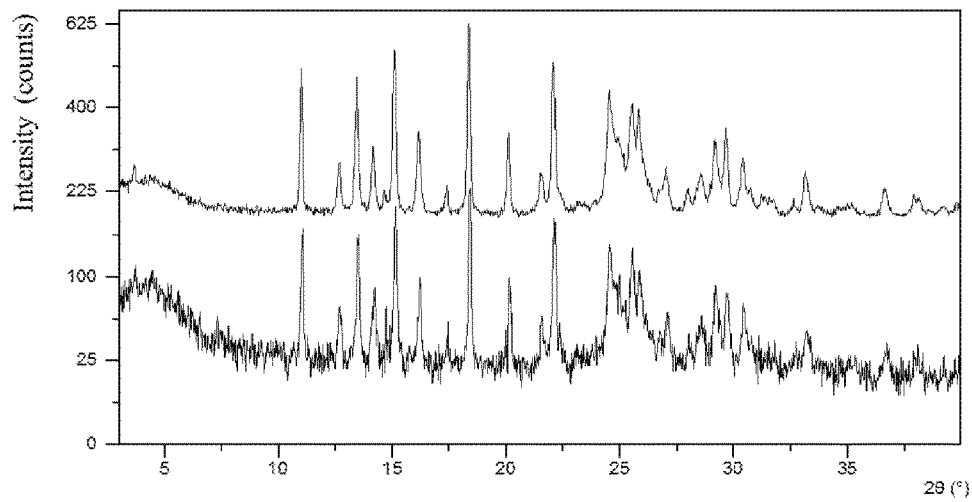
FIG. 11B shows an XRPD pattern overlay of Form CS2 of the present disclosure before and after being stored under 40° C./75% RH for one month (top: XRPD pattern before storage, bottom: XRPD pattern after storage).
Figure 11C:
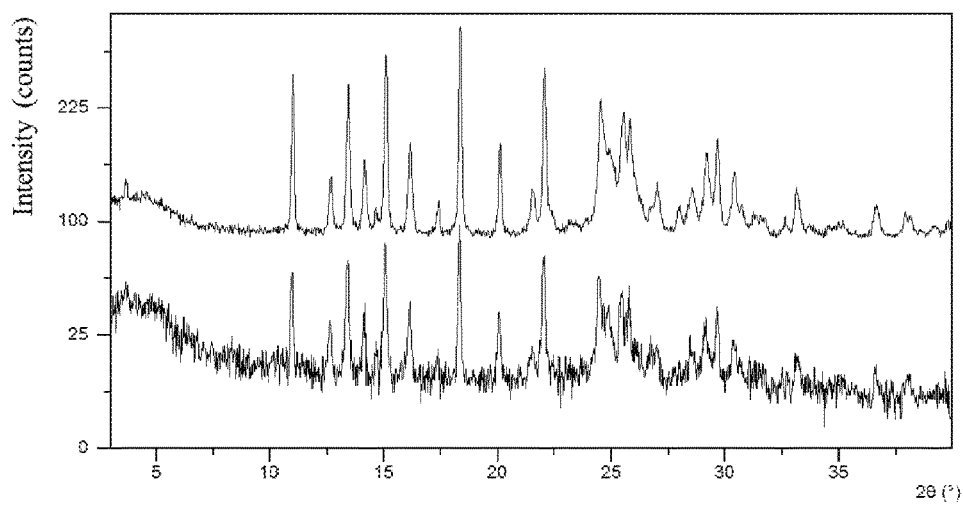
FIG. 11C shows an XRPD pattern overlay of Form CS2 of the present disclosure before and after being stored under 60° C./75% RH for one month (top: XRPD pattern before storage, bottom: XRPD pattern after storage).

| Initial Form | Condition | Time | Solid Form |
|---|---|---|---|
| Form CS2 | 25° C./60% RH | 1 month | Form CS2, no form change (as shown in FIG. 11A) |
|  | 40° C./75% RH | 1 month | Form CS2, no form change (as shown in FIG. 11B) |
|  | 60° C./75% RH | 1 month | Form CS2, no form change (as shown in FIG. 11C) |

Figure 12:
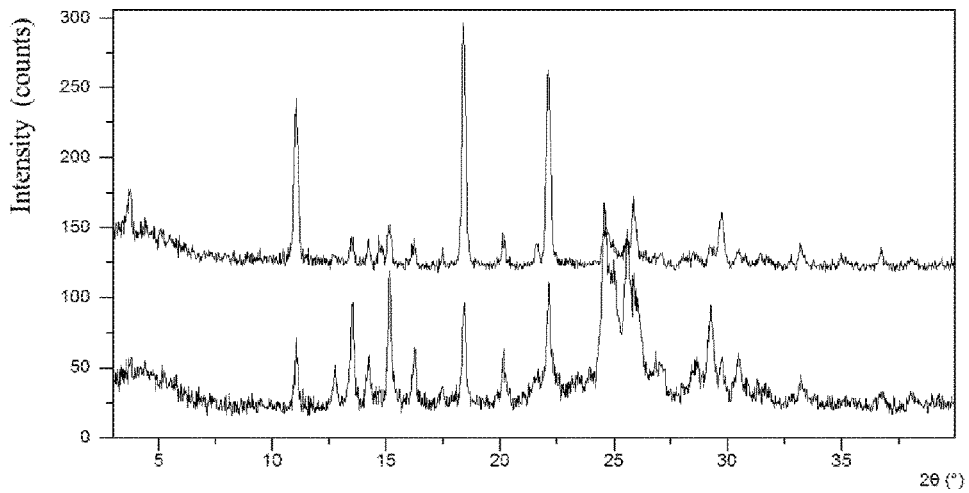
FIG. 12 shows an XRPD pattern overlay of Form CS2 before and after grinding (top: XRPD pattern before storage, bottom: XRPD pattern after grinding).

Mechanical stability experiment: Form CS2 was manually ground for 5 minutes in a mortar. The XRPD pattern collected before and after grinding is depicted in FIG. 12.

EXAMPLE 10

Hygroscopicity of Form CS2

Dynamic vapor sorption (DVS) was applied to test hygroscopicity of Form CS2 with 10 mg of sample. The weight gain of Form CS2 from 40% RH to 80% RH is 0.11%, which means Form CS2 is low hygroscopic.

EXAMPLE 11

Pressure Stability of Form CS2

Figure 15:
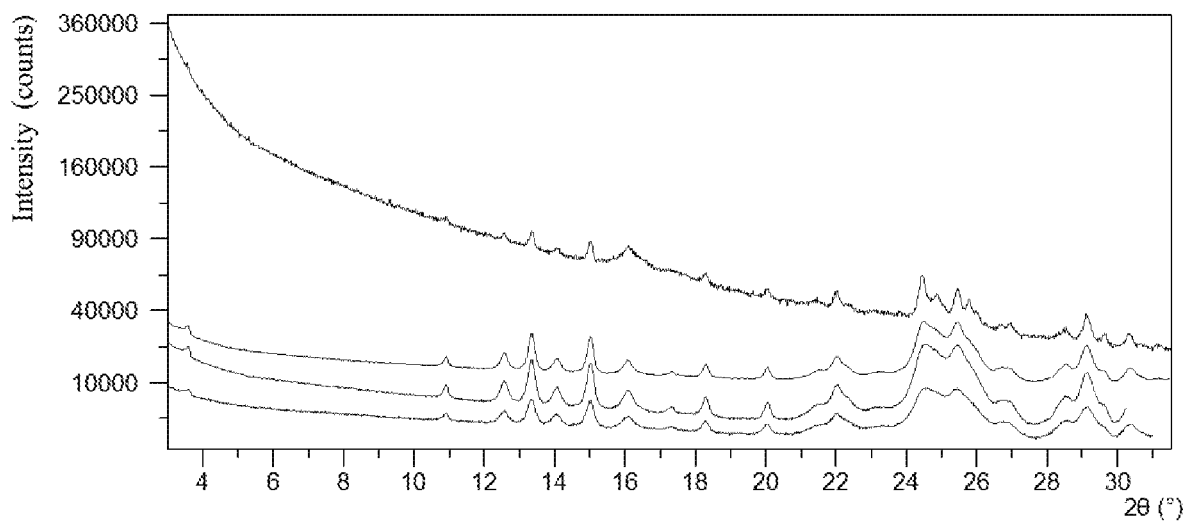
FIG. 15 shows an XRPD pattern overlay of Form CS2 of pressure stability (from top to bottom: XRPD pattern before tableting, XRPD pattern after tableting under 3 KN pressures, XRPD pattern after tableting under 7 KN pressures, XRPD pattern after tableting under 14 KN pressures).

Form CS2 was compressed using an ENERPAC manual tablet press under 3 KN, 7 KN and 14 KN pressure with φ6 mm round tooling (to ensure isotropy of the tablet). XRPD pattern overlay depicted in FIG. 15 was collected by a Bruker Panalytical Empyrean X-ray diffractometer before and after tableting. There was no form change after tableting, which means Form CS2 has good pressure stability.

EXAMPLE 12

Preparation of Form CS2 Drug Product

Form CS2 and excipients were blended according to formulation in Table 10 and tablet was compressed using an ENERPAC manual tablet press under 10 KN pressure with φ6 mm round tooling.

The tablets were stored in HDPE bottles under 30° C./65% RH condition for 3 months to evaluate tablet stability. The crystalline form of the sample was tested at the end of 3 months, and the result show that Form CS2 drug product keeps stable for at least 3 months under 30° C./65% RH condition.

TABLE 10

| Tablet ingredients | Dosage mg/tablet |
|---|---|
| API (CS2) | 32.00 |
| Microcrystalline cellulose (PH105250) | 56.86 |
| Carboxymethyl starch sodium (DST) | 7.00 |
| Sodium dodecyl sulfate | 1.00 |
| Polyvinylpyridone (Povidone K29/32) | 2.69 |
| Silica (colloid) (AEROSIL 200 Pharma) | 0.25 |
| Magnesium stearate (5712) | 0.20 |
| Total | 100.00 |

EXAMPLE 13

Preparation of Form CS8

8.3 mg of vadadustat was weighted into a 1.5 mL glass vial and 0.65 mL of mixed solvent of acetone and water (6:7, v/v) was added into the vial to form a clear solution at 50° C. The clear solution was then transferred to 5° C. and stirred overnight, and solid precipitation was observed.

According to the test results, the solid obtained in Example 13 was confirmed to be Form CS8.

Figure 8:
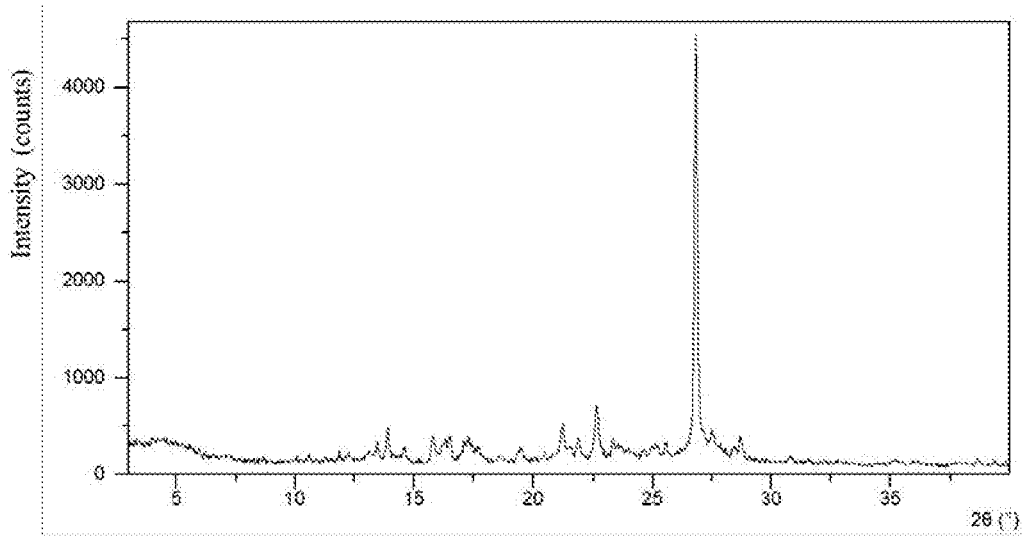
FIG. 8 shows an XRPD pattern of Form CS8 according to example 8 of the present disclosure.

The XRPD data are listed in Table 11, and the XRPD pattern is depicted in FIG. 8.

Figure 9:
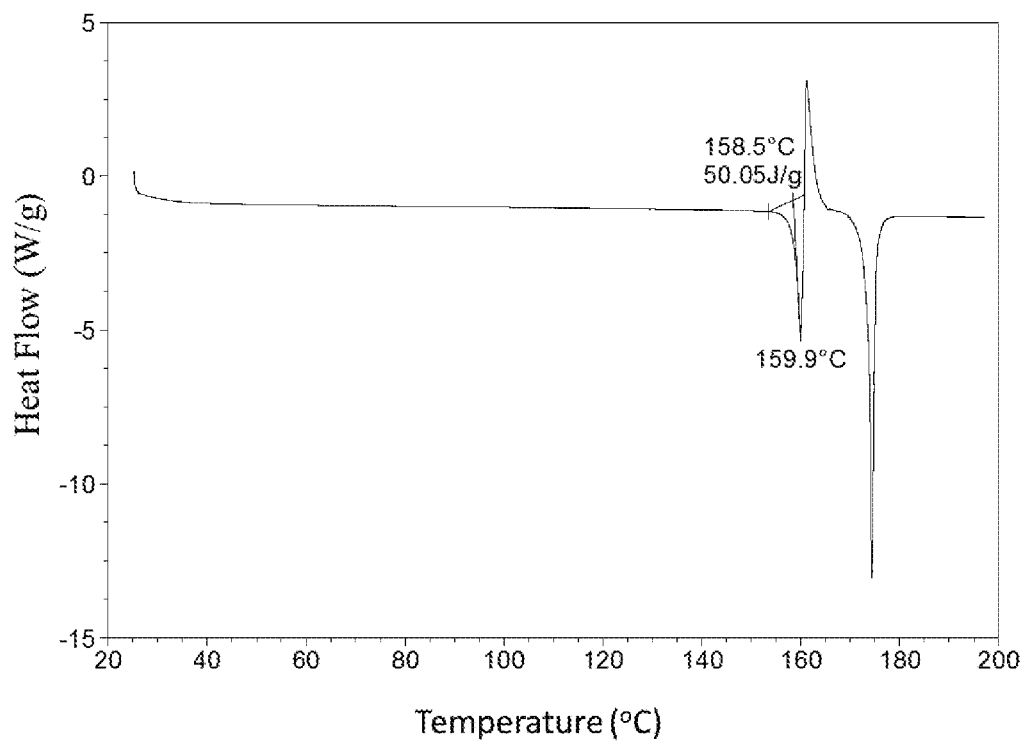
FIG. 9 shows a DSC curve of Form CS8 according to example 8 of the present disclosure.

The DSC curve of Form CS8 is depicted in FIG. 9.

TABLE 11

| 2θ | d spacing | Intensity % |
|---|---|---|
| 10.58 | 8.36 | 1.13 |
| 11.87 | 7.45 | 1.95 |
| 12.31 | 7.19 | 2.02 |
| 13.48 | 6.57 | 4.77 |
| 13.92 | 6.36 | 7.95 |
| 14.61 | 6.06 | 2.87 |
| 15.81 | 5.60 | 6.28 |
| 16.52 | 5.37 | 5.64 |
| 17.22 | 5.15 | 4.83 |
| 18.63 | 4.76 | 1.41 |
| 19.48 | 4.56 | 3.31 |
| 20.48 | 4.34 | 2.20 |
| 21.23 | 4.19 | 9.24 |
| 21.89 | 4.06 | 5.59 |
| 22.64 | 3.93 | 13.38 |
| 23.34 | 3.81 | 5.54 |
| 23.55 | 3.78 | 3.72 |
| 25.11 | 3.55 | 3.70 |
| 25.54 | 3.49 | 4.93 |
| 26.81 | 3.33 | 100.00 |
| 27.52 | 3.24 | 6.82 |
| 28.68 | 3.11 | 4.96 |
| 35.15 | 2.55 | 1.02 |
| 38.66 | 2.33 | 1.03 |
| 39.33 | 2.29 | 0.74 |

EXAMPLE 14

Dynamic Solubility of Form CS8

Certain amount of Form CS8 in the present disclosure and Form A in WO2015073779 was weighted into vials and then suspended in SGF (Simulated gastric fluids) and water. The systems were rotated on the rotator at a rate of 25 r/min. After equilibrated for 1 h, 4 h and 24 h, the suspension was separated through 0.45 μm PTFE centrifugal filter and the filtrate was collected. The concentration of the filtrates was measured by HPLC. The results are listed in Table 12, 13.

TABLE 12

| | Solubility | |
|---|---|---|
| | Solubility in SGF (mg/mL) | |
| Time | Form CS8 | Form A in WO2015073779 |
| 1 h | 0.020 | 0.0085 |
| 4 h | 0.022 | 0.0086 |
| 24 h | 0.033 | 0.0038 |

TABLE 13

| | Solubility | |
|---|---|---|
| | Solubility in SGF (mg/mL) | |
| Time | Form CS8 | Form A in WO2015073779 |
| 4 h | 0.10 | 0.057 |
| 24 h | 0.15 | 0.093 |

The results show that the solubility of Form CS8 in the present disclosure in SGF and water at 1 h, 4 h and 24 h is higher than that of Form A in WO2015073779.

EXAMPLE 15

Stability of Form CS8

Form CS8 of the present disclosure was stored under 25° C./60% RH, 40° C./75% RH and 60° C./75% RH for 20 days. The XRPD pattern was collected before and after storage, and the results are shown in Table 14.

TABLE 14

| Initial Form | Condition | Time | Solid Form |
|---|---|---|---|
| Form CS2 | 25° C./60% RH | 20 days | Form CS8, no form change |
| | 40° C./75% RH | 20 days | Form CS8, no form change |
| | 60° C./75% RH | 20 days | Form CS8, no form change |

The results show that Form CS8 keeps stable for at least 20 days under 25° C./60% RH, 40° C./75% RH and 60° C./75% RH conditions. It can be seen that Form CS8 in the present disclosure has good stability.

EXAMPLE 16

Hygroscopicity of Form CS8

Figure 14:
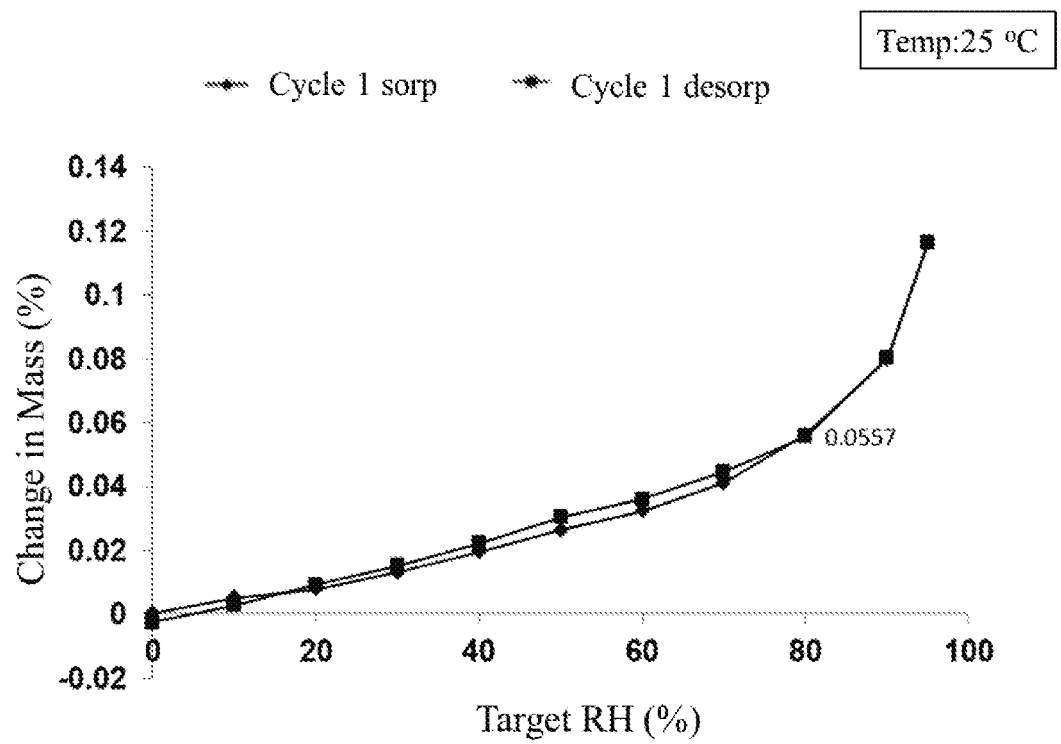
FIG. 14 shows a DVS plot of Form CSB.

Dynamic vapor sorption (DVS) was applied to test hygroscopicity of Form CS8 with 10 mg of sample and the DVS curve is depicted in FIG. 14. The weight gain of Form CS8 under 80% RH is 0.06%, which means Form CS8 is non hygroscopic or almost non hygroscopic.

Description and definition of hygroscopicity in the general principle 9103 of Chinese Pharmacopoeia:
  deliquescent: Sufficient water is absorbed to form a liquid;
  very hygroscopic: Increase in mass is equal to or greater than 15 percent;
  hygroscopic: Increase in mass is less than 15 percent and equal to or greater than 2 percent;

slightly hygroscopic: Increase in mass is less than 2 percent and equal to or greater than 0.2 percent.

non hygroscopic or almost non hygroscopic: Increase in mass is less than 0.2%.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form CS1 of {[5-(3-chlorophenyl)-3-hydroxypyridine-2-carbonyl] amino} acetic acid, wherein the X-ray powder diffraction pattern shows characteristic peaks at 2theta values of 13.9°±0.2°, 15.3°±0.2°, 15.6°±0.2° and 26.8°±0.2° using CuKα radiation.

2. The crystalline form CS1 according to claim 1, wherein the X-ray powder diffraction pattern shows one or more characteristic peaks at 2theta values of 17.0°±0.2°, 19.1°±0.2°, 23.5°±0.2° and 25.6°±0.2° using CuKα radiation.

3. A process for preparing crystalline form CS1 according to claim 1, wherein crystalline form CS1 is obtained from either one of the following methods:
   1) Dissolving {[5-(3-chlorophenyl)-3-hydroxypyridine-2-carbonyl] amino} acetic acid into ethers and then evaporating at room temperature to obtain solids; or
   2) Dissolving {[5-(3-chlorophenyl)-3-hydroxypyridine-2-carbonyl] amino} acetic acid into tetrahydrofuran, and then adding water slowly into the solution or adding the solution into water; Stirring at room temperature for a period of time; Filtering and drying to obtain solids.

4. The process for preparing crystalline form CS1 according to claim 3, wherein said ether is methyl tert-butyl ether; said stirring time is 1-48 h.

5. A crystalline form CS2 of {[5-(3-chlorophenyl)-3-hydroxypyridine-2-carbonyl] amino} acetic acid, wherein the X-ray powder diffraction pattern shows characteristic peaks at 2theta values of 14.1°±0.2°, 15.0°±0.2° and 18.3°±0.2° using CuKα radiation.

6. The crystalline form CS2 according to claim 5, wherein the X-ray powder diffraction pattern shows one or two or three characteristic peaks at 2theta values of 12.6°±0.2°, 13.4°±0.2° and 22.0°±0.2° using CuKα radiation.

7. The crystalline form CS2 according to claim 5, wherein the X-ray powder diffraction pattern shows one or two or three characteristic peaks at 2theta values of 10.9°±0.2°, 16.1°±0.2° and 20.1°±0.2° using CuKα radiation.

8. A process for preparing crystalline form CS2 according to claim 5, wherein crystalline form CS2 is obtained by dissolving {[5-(3-chlorophenyl)-3-hydroxypyridine-2-carbonyl] amino} acetic acid into ketones or 1,4-dioxane or dimethyl sulfoxide (DMSO), and then adding water slowly into the solution or adding the solution into water, stirring at room temperature for a period of time, filtering and drying to obtain solids.

9. The process for preparing crystalline form CS2 according to claim 8, wherein said ketone is acetone, said stirring time is 1-48 h.

10. A crystalline form CS8 of {[5-(3-chlorophenyl)-3-hydroxypyridine-2-carbonyl] amino} acetic acid, wherein the X-ray powder diffraction pattern shows characteristic peaks at 2theta values of 21.2°±0.2°, 22.6°±0.2° and 26.8°±0.2° using CuKα radiation.

11. The crystalline form CS8 according to claim 10, wherein the X-ray powder diffraction pattern shows one or more characteristic peaks at 2theta values of 13.5°±0.2°, 13.9°±0.2°, 15.8°±0.2°, 21.9°±0.2° and 28.7°±0.2° using CuKα radiation.

12. A process for preparing crystalline form CS8 according to claim 10, wherein crystalline form CS8 is obtained by dissolving {[5-(3-chlorophenyl)-3-hydroxypyridine-2-carbonyl] amino} acetic acid into a mixture of water and ketones, placing the clear solution at 5° C. and stirring for a period of time, filtering and drying to obtain solids.

13. The process for preparing crystalline form CS8 according to claim 12, wherein said dissolving temperature is 40-56° C., said ketone is acetone, said volume ratio of acetone and water is 1:3-2:1, said stirring time is 8-48 h.

14. A pharmaceutical composition, wherein said pharmaceutical composition comprises a therapeutically effective amount of crystalline form CS1 according to claim 1, and pharmaceutically acceptable carriers, diluents or excipients.

15. A method for treating anemia, comprising administering to a patient in need thereof a therapeutically effective amount of crystalline form CS1 according to claim 1.

16. A method for treating anemia caused by chronic kidney disease, comprising administering to a patient in need thereof a therapeutically effective amount of crystalline form CS2 according to claim 5.

17. A pharmaceutical composition, wherein said pharmaceutical composition comprises a therapeutically effective amount of crystalline form CS2 according to claim 5, and pharmaceutically acceptable carriers, diluents or excipients.

18. A pharmaceutical composition, wherein said pharmaceutical composition comprises a therapeutically effective amount of crystalline form CS8 according to claim 10, and pharmaceutically acceptable carriers, diluents or excipients.

19. A method for treating anemia, comprising administering to a patient in need thereof a therapeutically effective amount of crystalline form CS2 according to claim 5.

20. A method for treating anemia, comprising administering to a patient in need thereof a therapeutically effective amount of crystalline form CS8 according to claim 10.

* * * * *